US006730380B2

(12) United States Patent
Littleton et al.

(10) Patent No.: US 6,730,380 B2
(45) Date of Patent: *May 4, 2004

(54) READILY-DONNED ELASTOMERIC ARTICLES

(75) Inventors: Kermit R. Littleton, Julian, CA (US); Ronald Gloriani, Murrieta, CA (US); Garth Brown, Alpine, CA (US); Jason Baker, La Costa, CA (US); K C Nguyen, Murrieta, CA (US); Jali Lamar Williams, San Luis Obispo, CA (US)

(73) Assignee: Safeskin Corp., Roswell, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 83 days.

(21) Appl. No.: 09/133,056

(22) Filed: Aug. 11, 1998

(65) Prior Publication Data

US 2002/0015812 A1 Feb. 7, 2002

Related U.S. Application Data

(63) Continuation-in-part of application No. 08/604,009, filed on Feb. 20, 1996, now Pat. No. 5,792,531.

(51) Int. Cl.[7] .............................. B32B 1/08; B32B 1/10; A41D 19/015; A41D 27/02
(52) U.S. Cl. ........................... 428/36.8; 2/161.7; 2/168; 428/36.91; 428/521; 428/522
(58) Field of Search ................................. 428/500, 521, 428/523, 35.7, 36.91, 36.92, 36.8, 516, 517, 519, 522; 2/161.7, 168

(56) References Cited

U.S. PATENT DOCUMENTS

| 2,872,427 A | 2/1959 | Schroeder .................. 260/29.2 |
| 3,286,011 A | 11/1966 | Kavalir et al. ............... 264/306 |
| 3,411,982 A | 11/1968 | Kavalir et al. ............... 161/242 |
| 3,566,874 A | 3/1971 | Shepherd et al. ........... 128/349 |
| 3,740,262 A | 6/1973 | Agostinelli .................. 117/94 |

(List continued on next page.)

FOREIGN PATENT DOCUMENTS

| EP | 0455323 A2 | 11/1991 |
| EP | 356580 B1 | 6/1995 |
| EP | 543657 B1 | 1/1996 |
| EP | 854174 A1 | 7/1998 |
| GB | 2270618 A | 3/1994 |
| JP | 6-340758 A | * 12/1994 |
| WO | 8904647 | 6/1989 |
| WO | WO92/13497 | 8/1992 |
| WO | WO94/20574 | 9/1994 |

OTHER PUBLICATIONS

Derwent Abstract of JP 6–340578 A; Suzuki; Surface treatment of rubber gloves to provide good gripping properties.*

(List continued on next page.)

*Primary Examiner*—Sandra M. Nolan
(74) *Attorney, Agent, or Firm*—Dority & Manning, P.A.

(57) ABSTRACT

An elastomeric article such as a glove includes a substrate body made of an styrene-ethylene-butylene-styrene block copolymer, and a donning layer overlying at least one side of the substrate body. The donning layer is formed of 1,2 polybutadiene, preferably syndiotactic 1,2 polybutadiene, or a chlorinated mid block unsaturated block copolymer. Optionally, a surfactant layer is present over the donning layer to further improve the donning characteristics. The surfactant layer is preferably an alkyl dimethylbenzyl quaternary, an alkyl trimethyl quaternary, a dialkyl dimethyl quaternary, sodium lauryl sulfate, or pyridinium chloride.

22 Claims, 4 Drawing Sheets

U.S. PATENT DOCUMENTS

| | | | |
|---|---|---|---|
| 3,813,695 A | 6/1974 | Podell, Jr. et al. ............... 2/168 |
| 3,896,807 A | 7/1975 | Buchalter |
| 3,919,442 A | 11/1975 | Esemplare et al. ......... 428/494 |
| 3,933,723 A | 1/1976 | Grenness ................... 260/33.6 |
| 3,992,221 A | 11/1976 | Homsy et al. ................. 134/16 |
| 4,027,060 A | 5/1977 | Esemplare et al. ......... 428/212 |
| 4,061,709 A | 12/1977 | Miller et al. ................. 264/293 |
| 4,070,713 A | 1/1978 | Stockum |
| 4,082,862 A | 4/1978 | Esemplare et al. ......... 427/433 |
| 4,143,109 A | 3/1979 | Stockum ..................... 264/112 |
| 4,154,712 A | 5/1979 | Lee, Jr. ..................... 260/29.1 |
| 4,190,685 A * | 2/1980 | Hart et al. ................... 427/302 |
| 4,218,779 A * | 8/1980 | Hart et al. ..................... 2/168 |
| 4,248,751 A | 2/1981 | Willing ..................... 260/29.2 |
| 4,255,296 A | 3/1981 | Ogawa et al. ................. 260/5 |
| 4,302,852 A | 12/1981 | Joung ............................ 2/167 |
| 4,304,008 A | 12/1981 | Joung ............................ 2/167 |
| 4,310,928 A | 1/1982 | Joung ............................ 2/161 |
| 4,331,738 A | 5/1982 | Kuan ......................... 428/494 |
| 4,354,001 A | 10/1982 | Kuan ......................... 524/501 |
| 4,394,473 A | 7/1983 | Winter et al. ............... 524/276 |
| 4,450,152 A | 5/1984 | Ona et al. ..................... 424/70 |
| 4,478,903 A | 10/1984 | Kishida et al. ............. 428/216 |
| 4,482,577 A | 11/1984 | Goldstein et al. ............... 427/2 |
| 4,499,154 A | 2/1985 | James et al. ................ 428/494 |
| 4,548,844 A | 10/1985 | Podell et al. ................. 428/35 |
| 4,563,347 A | 1/1986 | Starch .......................... 424/70 |
| 4,575,476 A | 3/1986 | Podell et al. ............... 428/494 |
| 4,589,873 A | 5/1986 | Schwartz et al. ........... 604/265 |
| 4,597,108 A | 7/1986 | Momose ........................ 2/168 |
| 4,597,962 A | 7/1986 | Grollier et al. ............... 424/47 |
| 4,631,187 A | 12/1986 | Padden et al. ................. 424/70 |
| 4,645,809 A | 2/1987 | Bell ............................. 52/140 |
| 4,670,500 A | 6/1987 | Gupta ..................... 524/41.47 |
| 4,751,275 A | 6/1988 | Witte et al. ................. 521/134 |
| 4,779,290 A * | 10/1988 | Welch et al. ............... 2/161 R |
| 4,790,365 A * | 12/1988 | Sandstrom et al. ......... 152/510 |
| 4,851,266 A | 7/1989 | Momose et al. ............ 427/353 |
| 4,902,741 A | 2/1990 | Burroway et al. .......... 524/836 |
| 4,910,013 A | 3/1990 | Kanamaru et al. ............ 424/47 |
| 4,950,468 A | 8/1990 | Nakamura et al. ............ 424/70 |
| 4,987,893 A | 1/1991 | Salamone et al. .......... 128/156 |
| 5,011,896 A | 4/1991 | Bell et al. .................... 526/927 |
| 5,019,096 A * | 5/1991 | Fox, Jr. et al. ................. 623/1 |
| 5,021,381 A | 6/1991 | Burroway et al. .......... 502/117 |
| 5,053,048 A | 10/1991 | Pinchuk ......................... 623/1 |
| 5,069,965 A | 12/1991 | Esemplare .................. 428/330 |
| 5,084,514 A * | 1/1992 | Szczechura ................. 525/123 |
| 5,088,125 A | 2/1992 | Ansell et al. ..................... 2/167 |
| 5,103,812 A | 4/1992 | Salamone et al. ............ 602/52 |
| 5,112,900 A | 5/1992 | Buddenhagen et al. ..... 524/484 |
| 5,126,126 A | 6/1992 | Varaprath et al. ............. 424/71 |
| 5,133,090 A | 7/1992 | Modak et al. ................ 42/168 |
| 5,154,759 A | 10/1992 | Cifuentes et al. ............. 106/3 |
| 5,160,449 A | 11/1992 | Halloran ...................... 424/70 |
| 5,164,522 A | 11/1992 | McCarthy et al. ........... 554/139 |
| 5,183,845 A | 2/1993 | Parkinson et al. .......... 524/726 |
| 5,244,728 A | 9/1993 | Bowman et al. ............ 428/360 |
| 5,260,055 A | 11/1993 | Imperante et al. ............ 424/71 |
| 5,272,012 A | 12/1993 | Opolski ................... 428/423.1 |
| 5,272,771 A | 12/1993 | Ansell et al. ................. 25/167 |
| 5,278,263 A | 1/1994 | Burroway .................... 526/94 |
| 5,284,607 A | 2/1994 | Chen ........................... 264/37 |
| 5,332,612 A | 7/1994 | Payet et al. ................. 428/148 |
| 5,338,565 A | 8/1994 | Shlenker et al. ........... 427/2.25 |
| 5,356,549 A | 10/1994 | Takahashi et al. ......... 252/49.6 |
| 5,405,666 A | 4/1995 | Brindle ...................... 428/36.4 |
| 5,407,715 A | 4/1995 | Buddenhagen et al. .... 428/35.7 |
| 5,415,857 A | 5/1995 | Robbins et al. ........ 424/70.122 |
| 5,443,744 A | 8/1995 | Bloch et al. ................ 252/32.7 |
| 5,444,121 A | 8/1995 | Grennes et al. ................ 525/89 |
| 5,451,439 A | 9/1995 | Bigg ......................... 428/36.8 |
| 5,458,588 A | 10/1995 | Amdur et al. ............... 604/349 |
| 5,468,822 A | 11/1995 | Tsujimoto et al. ....... 526/340.1 |
| 5,474,835 A | 12/1995 | McCarthy et al. .......... 428/224 |
| 5,518,533 A | 5/1996 | Howe ............................ 106/3 |
| 5,520,908 A | 5/1996 | Lundmark ................. 424/70.1 |
| 5,534,350 A | 7/1996 | Liou ....................... 428/423.1 |
| 5,564,127 A | 10/1996 | Manne ........................ 2/161.7 |
| 5,567,428 A | 10/1996 | Hughes ....................... 424/401 |
| 5,570,475 A | 11/1996 | Nile et al. ................... 2/161.7 |
| 5,571,219 A * | 11/1996 | Gorton ....................... 2/161.7 |
| 5,578,298 A | 11/1996 | Berthiaume et al. ... 424/70.122 |
| 5,620,773 A | 4/1997 | Nash .......................... 428/145 |
| 5,649,326 A | 7/1997 | Richard, Jr. et al. ......... 2/161.7 |
| 5,677,400 A | 10/1997 | Tsujimoto et al. ............ 526/94 |
| 5,691,069 A | 11/1997 | Lee ............................. 428/500 |
| 5,716,443 A | 2/1998 | Kijima et al. .......... 106/287.11 |
| 5,736,591 A * | 4/1998 | Dunn ......................... 523/122 |
| 5,742,943 A | 4/1998 | Chen ............................ 2/168 |
| 5,792,531 A | 8/1998 | Littleton et al. |
| 5,881,386 A | 3/1999 | Horwege et al. ............. 2/161.7 |
| 5,939,485 A | 8/1999 | Bromberg et al. .......... 524/556 |
| 5,965,610 A | 10/1999 | Modak et al. ............... 514/494 |
| 5,986,026 A | 11/1999 | Wong et al. .............. 526/123.1 |
| 5,993,923 A | 11/1999 | Lee ............................ 428/36.8 |
| 6,016,570 A | 1/2000 | Vande Pol et al. ........... 2/161.9 |
| 6,306,514 B1 | 10/2001 | Weikel et al. |

OTHER PUBLICATIONS

Polymer Science Dictionary, 2nd Edition; Edited by Mark Alger, pp. 397–398.*

Weikel et al., Publ. No. US 2002/0009561 A1, Jan. 24, 2002.

R.D. Swisher "Surfactant Biodegradation,", (no name, publication; no date given).

Final Report on the Safety Assessment of Certrimonium Chloride; Cetrimonium Bromide, and Steartrimonium Chloride *Cosmetic Ingredient Review* vol. 16, No. 3, [no page Nos. given].

"Cationic Surfactants"; Jun., 1997, [no page nos. given] James, P.H. Ogden, and J.M. Wates; A.D. Azko Chemie UK Limited, Oba, UK [No name, publication or date given].

"Interactions of Surfactants with Polymers and Proteins;" pp. 10, 11, 22 and 23 [No month, publication date given].

Rieger, Factors Affecting Sorption of Topically Applied Substances, pp 57–58 & 264, [No publn or date given].

L.D. Rhein, C.R. Robbins, K. Fernee and R. Cantore; "Surfactant Structure Effects on Swelling of Isolated Human Stratum Corneum"; *J. Soc. Cosmet. Chem 37*, pp. 125–139 (May, Jun. 1986).

George V. Scott, Ph.D., Clarence R. Robbins, Ph.D., and James D. Barnhurst, Ph.D. "Sorption of Quaternary Ammonium Surfactants by Human Hair"; *J. Soc. Cosmetic Chemistry 20*, pp. 135–152 (Feb. 1969).

Ruth B. Kundsin, M.A. & Carl W. Walter, M.D., "Investigations on Adsorption of Benzalkonium Chloride U.S.P. by Skin, Gloves, and Sponges"; *AMA Archives Of Surgery, 75*, pp. 1036–1042 (Dec. 1957).

Incroquat Behenyl TMS; Japanese Approval Submission, [no pbln, date given, no page Nos.].

A.D. Roberts et al., "Surface Treatments to Reduce Friction: Rubber Glove Applications," *Rubber Chemistry and Technology*, vol. 63, pp. 722–733 (1990).

* cited by examiner

READILY-DONNED ELASTOMERIC ARTICLES

This application is a continuation in part of application Ser. No. 08/604,009, filed Feb. 20, 1996, now U.S. Pat. No. 5,792,531, for which priority is claimed.

BACKGROUND OF THE INVENTION

This invention relates to elastomeric articles such as gloves, and, more particularly, to such elastomeric articles specially treated to make them easy to slip on.

Highly elastic articles such as surgical and examination gloves have traditionally been made of natural rubber latex in order to utilize its combination of good elasticity and strength. However, some persons are allergic to natural rubber latex, and in addition natural rubber latex is susceptible to environmental damage such as ozonation. For many years, the only available alternatives to natural rubber latex were synthetic elastomers which did not produce allergic reactions, but which also tended to exhibit insufficient elasticity and strength, as well as susceptibility to ozone degradation in some cases.

An important advance in this area was the development of medical gloves made of S-EB-S (styrene-ethylene-butylene-styrene) synthetic elastomer block copolymers, as disclosed in U.S. Pat. Nos. 5,112,900 and 5,407,715. Articles such as gloves are readily dip-formed from such block copolymers, without the occurrence of pinholes that can result from impurities found in natural rubber latex. The articles have substantially the same elastic and strength properties as natural rubber latex, are hypoallergenic, and are not subject to ozonation damage. Gloves made of S-EB-S block copolymers are available commercially from Tactyl Technologies, Inc., Vista, Calif.

Tightly fitting elastomeric articles such as gloves and condoms, whether made of natural or synthetic elastomers, can be difficult to don. The elastomer action of the material of construction, its friction with the skin of the user, and the perspiration on the body of the user act in combination to make it difficult to slip the article on. To overcome this problem, it has been conventional practice to apply a powdered lubricant to the surface that is to contact the body of the user, such as the inside of the glove. As an example, epichloro-hydrin treated maize crosslinked starch is a common powder applied to the inside of elastomeric gloves during manufacture, to permit them to be more readily slipped onto the hand of the user.

The use of a powdered lubricant on the elastomer is operable, but has drawbacks in specific situations such as the case of surgical gloves. If some of the powder escapes from the inside of the glove into the surgical environment, as for example if the glove is torn during the surgery, the powder may enter the surgical wound to cause further complications for the patient. The powder may carry infectious agents, or the patient may be allergic to the powder.

Various other techniques are known for use with surgical gloves to improve their donning characteristics. These techniques include, for example, manufacturing the glove from a modified latex, using an inner layer of a hydrophilic polymer, applying a slip coating to the inner surface of the glove, providing lubricating particles on the inner surface of the glove, and other approaches.

While these techniques for producing powder-free gloves are perhaps operable in their conventional applications, the present inventors have found that they are not fully satisfactory for use with gloves made of the synthetic S-EB-S block copolymers and some other materials of construction. There is, accordingly, a need for an improved approach for providing a powder-free article such as a glove with acceptable donning characteristics. The present invention fulfills this need, and further provides related advantages.

SUMMARY OF THE INVENTION

The present invention provides an elastomeric, powder-free article having excellent donning characteristics. The article is preferably made using a substrate of synthetic elastomer that exhibits good elasticity and strength, is hypoallergenic, is resistant to environmental degradation, is producible by dip forming, and is otherwise acceptable for use. These properties are not adversely affected by the treatment and structure that provide improved donning characteristics, both initially and after aging of the article. The treatment for improving the donning characteristics is fully compatible with the forming of the underlying substrate. The approach of the invention is operable with a wide variety of substrate materials including, but not limited to, those made of natural rubber latex and those made of S-EB-S block co-polymers such as those disclosed in U.S. Pat. Nos. 5,112,900 and 5,407,715.

In accordance with one aspect of the invention, an elastomeric article comprises a substrate body made of an elastomeric material such as natural rubber latex or a mid block saturated styrene block copolymer such as an styrene-ethylene-butylene-styrene block copolymer, and a donning layer overlying at least one side of the substrate body. The donning layer comprises 1,2 polybutadiene, preferably syndiotactic 1,2 polybutadiene. Optionally, a surfactant-containing layer overlies the donning layer and comprises a cationic surfactant, or a cationic surfactant and a silicone antifoam. Operable surfactant-containing layers comprise an alkyl dimethylbenzyl quaternary, an alkyl trimethyl quaternary, a dialkyl dimethyl quaternary, sodium lauryl sulfate, and/or pyridinium chloride. The silicone antifoam is preferably polydimethyl siloxane emulsion.

In accordance with another aspect of the invention, an elastomeric article comprises a substrate body made of an elastomeric material, preferably a mid block saturated styrene block copolymer such as an styrene-ethylene-butylene-styrene block copolymer, and a donning layer overlying at least one side of the substrate body. The donning layer comprises a chlorinated mid block unsaturated block copolymer such as a chlorinated styrene diene block copolymer, preferably chlorinated styrene-isoprene block copolymer. The styrene-isoprene block copolymer preferably has a polystyrene block content of from about 10 to about 20 percent by weight of the total copolymer weight and an end block polystyrene molecular weight of at least about 5,000 grams per mole. A surfactant-containing layer overlies the donning layer and comprises a cationic surfactant, or a cationic surfactant and a silicone antifoam. The cationic surfactant is preferably an alkyl dimethylbenzyl quaternary, an alkyl trimethyl quaternary, a dialkyl dimethyl quaternary, sodium lauryl sulfate, or pyridinium chloride. The silicone antifoam is preferably polydimethyl siloxane emulsion.

The elastomeric article is manufactured by preparing the substrate body made of an elastomeric material by any operable technique, most preferably dip forming. The donning layer is applied to the substrate body by any operable technique, most preferably by dipping the substrate body into a solution of the donning layer polymer, and thereafter chlorinating the donning layer. The surfactant layer is applied over the donning layer by any operable technique, most preferably by dipping the substrate body and overlying donning layer into a solution of the surfactant.

The elastomeric article of the invention has excellent elastic and strength properties, is readily manufactured, and can be donned easily without the presence of any powder. In the case of the preferred S-EB-S substrate body, the article is hypoallergenic and is resistant to environmental degradation such as ozonation. The donning layer does not crack or peel from the substrate body during storage or service. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIGS. 5A and 5B are representations of chemical structures, wherein FIG. 5A represents 1,2 polybutadiene, and FIG. 5B represents syndiotactic 1,2 polybutadiene.

DETAILED DESCRIPTION OF THE INVENTION

Figure 1:
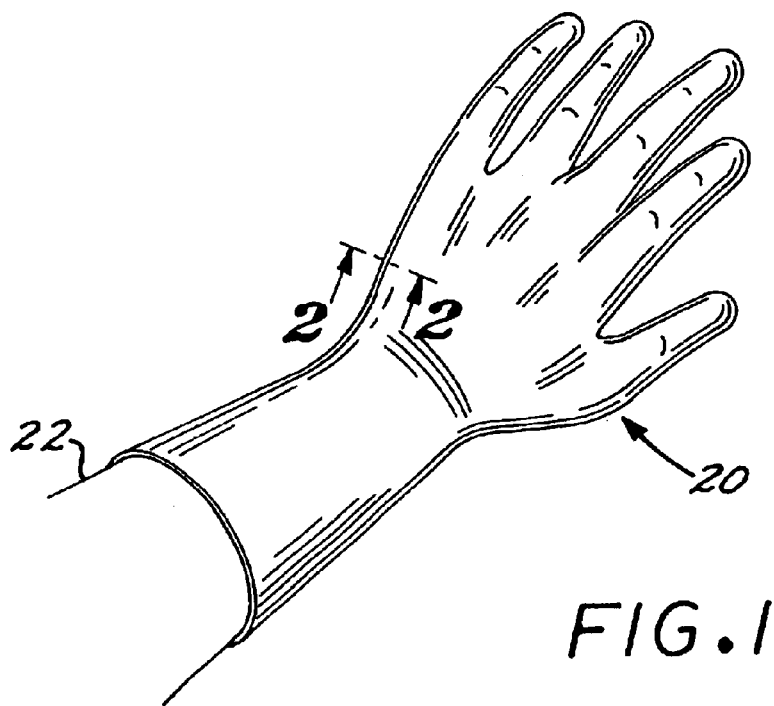
FIG. 1 is a perspective view of an elastomeric article made according to the invention.
Figure 2A:
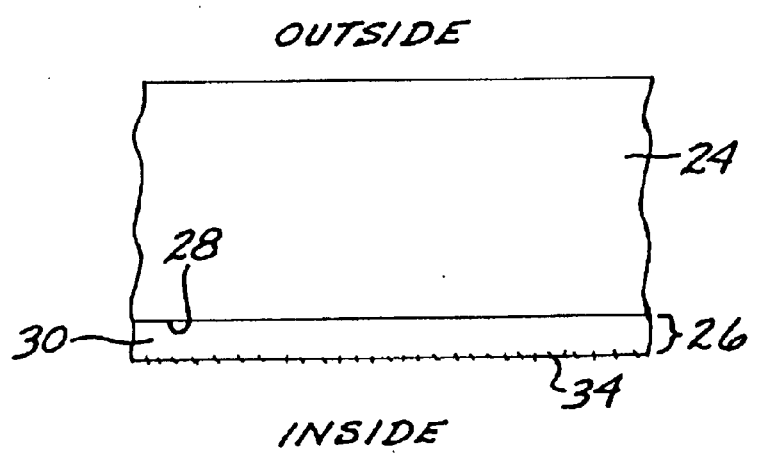
FIG. 2A is a sectional view through a first embodiment of the article of FIG. 1, taken generally along line 2—2.
Figure 2B:
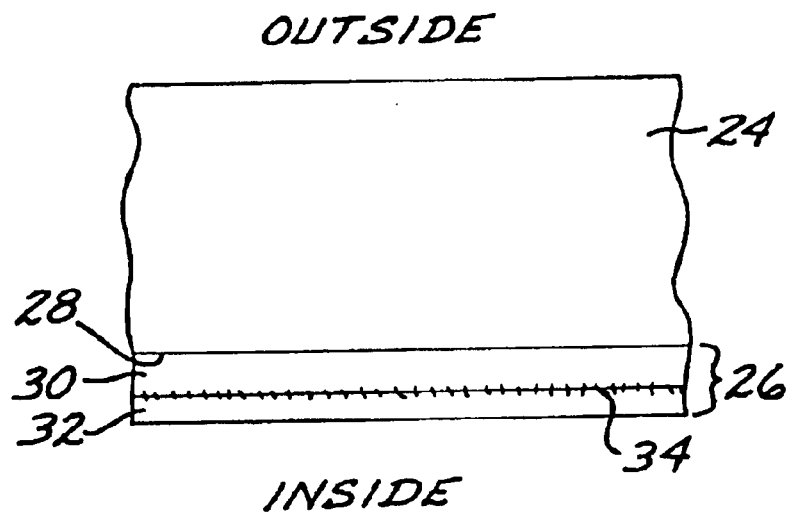
FIG. 2B is a sectional view through a second embodiment of the article of FIG. 1, taken generally along line 2—2.

FIG. 1 depicts an article made in accordance with the invention, in the preferred case a glove 20 on the hand of a user 22. FIGS. 2A and 2B illustrate the structure of two preferred embodiments of the glove 20. In both embodiments, the glove includes a substrate body 24 having the basic shape of the article, and a coating 26 on an inside surface 28 of the substrate body 24 that is to contact the body of the user 22 during service. The coating 26 includes a donning layer 30 overlying, contacting, and bonded to the substrate body 24. The embodiment of FIG. 2B further includes a surfactant layer 32, which also may be termed a lubricant layer, overlying and contacting the donning layer 30. FIGS. 2A and 2B are presented to illustrate the positions of the elements, and are not drawn to scale. The surfactant layer 32, for example, is typically at most only a few molecules thick.

The substrate body 24 is made of an elastomeric material, desirably comprising a synthetic elastomer including at least one styrene-ethylene-butylene-styrene (S-EB-S) block copolymer, and preferably a mixture of S-EB-S block copolymers. More preferably, the elastomeric material of the substrate body 24 includes a block copolymer component comprising at least two, and most preferably three, S-EB-S block copolymers. Each block copolymer has from about 25 to about 35 percent by weight of polystyrene blocks. The total mass of S-EB-S block copolymers has from about 40 to about 60 percent by weight of a first S-EB-S block copolymer with a solution viscosity of about 6500 cps at 25 percent by weight of copolymer in toluene at 77° F., from about 15 to about 59 percent by weight of a second S-EB-S block copolymer with a solution viscosity of about 2000 cps in toluene at 10 percent weight of polymer in toluene at 77° F., and from about 1 to about 40 percent by weight of a third S-EB-S block copolymer having a solution viscosity of about 1600 cps in toluene at 25 percent weight of polymer in toluene at 77° F. The most preferred elastomeric material further includes a plasticizer in an amount of from about 30 to about 65 parts by weight of the total mass of the S-EB-S block copolymer component. The article is fabricated by dipping a former into a liquid solution of the elastomer a sufficient number of times to build up the desired thickness on the former. This synthetic elastomeric material and the fabrication process are described more fully in U.S. Pat. Nos. 5,112,900 and 5,407,715, whose disclosures are incorporated by reference.

Figure 3:
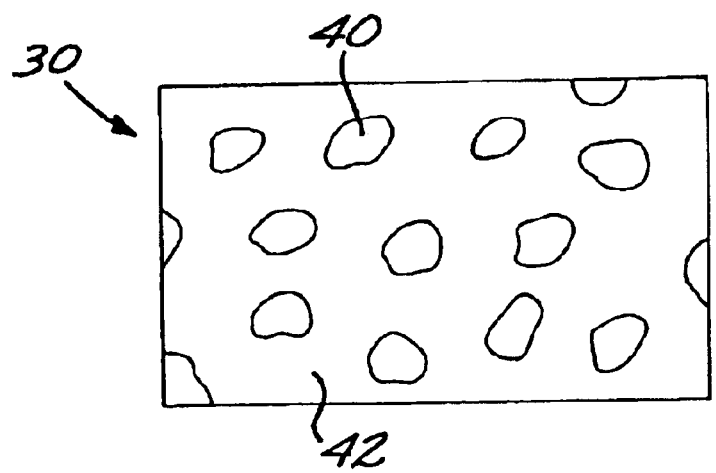
FIG. 3 is a schematic illustration of the microstructure of the styrene-isoprene-styrene material.

In one embodiment, the donning layer 30 comprises a chlorinated mid block unsaturated styrene-isoprene-styrene (S-I-S) block copolymer. The S-I-S block copolymer may include tri- or radial-blocks. The S-I-S block copolymer preferably has a polystyrene end block content of from about 10 to about 20 percent by weight, most preferably from about 15 to about 18 percent by weight, of the total weight of the S-I-S block copolymer. If the polystyrene end block content is below about 10 percent by weight, optimum strength properties are not achieved at higher temperatures. If the polystyrene end block content is above about 20 percent by weight, the treated surface of the article tends to be too smooth, promoting blocking and glare of the article, and also tends to stiffen the final article. Too high a polystyrene end block content is particularly to be avoided when the donning layer is used on a dip-formed substrate body. A further reason for selecting a maximum polystyrene end block content of about 20 percent by weight of the total S-I-S block copolymer is that this content produces a morphology of polystyrene domains 40 dispersed in a continuous polyisoprene matrix 42 in the donning layer 30, as illustrated in FIG. 3. This morphology results in good bonding of the donning layer 30 to the substrate body 24, both initially and after aging, and also imparts good elasticity to the donning layer so that it can stretch with the elastomer of the substrate body 24 without cracking. The donning layer also has good crack and peel resistance as a result of its composition and morphology. Polystyrene block contents greater than about 20 percent by weight result in a more agglomerated structure.

The molecular weight of the polystyrene end blocks is preferably at least about 5,000 grams per mole. It has been found that S-I-S block copolymers having polystyrene end blocks of molecular weight less than about 5,000 grams per mole have increased adhesion and blocking tendency, both initially and after heat aging. Blocking is the adhesion or sticking together of adjacent articles and, where present, causes the gloves to be difficult to open for insertion of the hand and also causes neighboring gloves to stick together in a package. A polystyrene end block molecular weight of more than about 5,000 grams per mole has been found to reduce this undesirable blocking, particularly when the substrate body is formed by a dip-forming technique.

Examples of suitable mid-block unsaturated S-I-S block copolymers include Kraton® D1107 available from Shell Chemical Co. and Vector® 511 and Vector® 4111 available from Dexco. The Vector® 4111 product, for example, contains 17.5–19.0 percent by weight styrene end blocks.

The material of the donning layer 30 can also be made of other polymers having reactive sites which can react with chlorine in the subsequent chlorination procedure. Elastomers having no such sites reactive with chlorine are not operable.

The donning layer 30 of mid block unsaturated S-I-S block copolymer has a chlorinated surface remote from the surface 28, indicated schematically at numeral 34 in FIGS. 2A and 2B. The chlorine atoms react with the mid-block (unsaturated) polyisoprene, modifying the tackiness of the layer slightly. Other halogens such as bromine or iodine may also be used, but are less preferred.

The surfactant layer 32 overlies the donning layer 30 in the embodiment of FIG. 2B. The surfactant layer 32 aids in donning the article when the user's body is either wet or dry and also reduces the tendency to blocking. The surfactant layer preferably comprises a cationic, an anionic, or a nonionic surfactant, and/or a silicone antifoam. Most preferably, the surfactant layer 32 is an alkyl dimethylbenzyl quaternary, an alkyl trimethyl quaternary, a dialkyl dimethyl quaternary, a pyridinium chloride such as cetyl pyridinium chloride, sodium lauryl sulfate, and/or polydimethyl siloxane emulsion, optionally mixed with silicone such as Dow Corning 365 emulsion or General Electric AF60. Examples of alkyl dimethylbenzyl quaternaries are steralkonium chloride and stearyl dimethylbenzyl ammonium chloride, such as the commercially available Varisoft SDC-85, Ammonyx 4002, Standamul 1002, and Mackernium SDC-85. An example of alkyl trimethyl quaternary is behentrimonium chloride, such as the commercially available Varisoft BT85. Examples of dialkyl dimethyl quaternaries are $C_{18}$–$C_{22}$ trimethyl ammonium methosulfate, such as the commercially available Varisoft BTMS, and disteryldimonium chloride, such as the commercially available Varisoft TA100.

By way of example, the substrate body 24 in the case of a glove produced by dip forming is preferably from about 0.004 to about 0.012 inches thick. The donning layer 30 cannot be readily expressed as having a thickness, but about 0.15 grams of the mid block unsaturated styrene-isoprene (SIS) block copolymer is used per glove. The chlorinated region 34 and the surfactant layer 32, where present, are more in the nature of surface treatments. These values are provided by way of illustration and not limitation.

Figure 4:
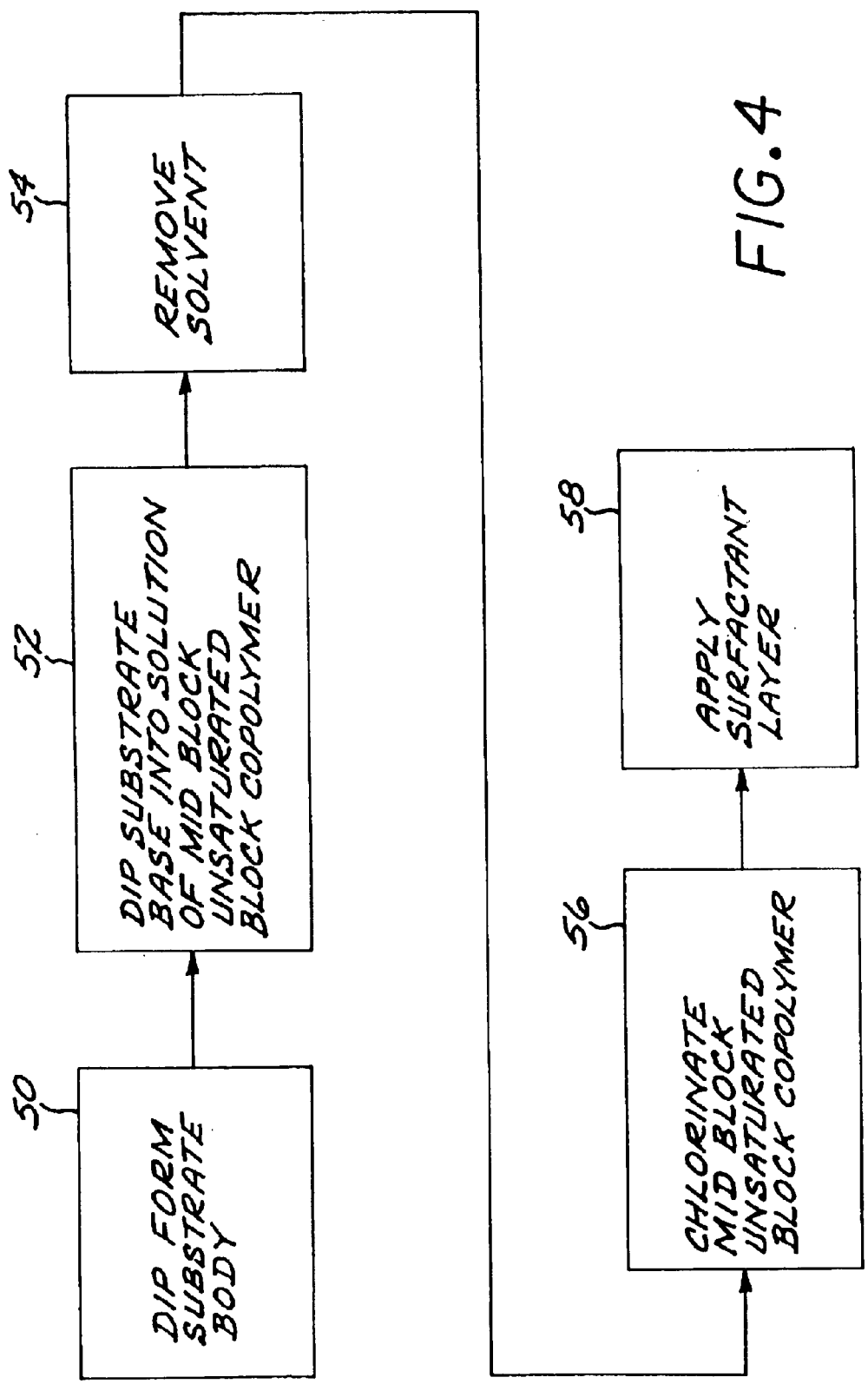
FIG. 4 is a block flow diagram for a preferred method of practicing the invention.

FIG. 4 illustrates the preferred approach for practicing this embodiment of the invention. The substrate body is prepared, preferably by dip forming, numeral 50. The preferred dip forming technique is discussed fully in U.S. Pat. Nos. 5,112,900 and 5,407,715. Briefly, the S-EB-S block copolymers are mixed with a plasticizer. The plasticizer is preferably a mineral oil, which is a refined petroleum paraffinic hydrocarbon oil. The preferred mineral oil has a specific gravity of 0.87 at 77° F., a viscosity of 170 centistokes at 77° F., and a Hirschler molecular weight of 492. The S-EB-S block copolymers are furnished by the manufacturer as a solid. To form a solution from which articles can be dip formed, the S-EB-S block copolymers and the mineral oil plasticizer are dissolved in a mutual solvent, preferably toluene. Toluene solutions of S-EB-S provide minimal viscosities of concentrated solutions compared to many other solvents. A highly concentrated solution improves dip-forming process economics by reducing the amount of solvent that must be processed in a solvent recovery operation. The S-EB-S in toluene solution is a true, stable solution, as distinct from a mixture or an emulsion. The process requires attaining such a solution, as by using a high shear mixer and mixing for a sufficient time to reach a homogeneous solution. The solution is filtered to remove any fine particulate matter.

To prepare the glove by dip forming, a sufficiently large amount of the S-EB-S elastomer solution is prepared in the manner described and placed into a dipping tank, at ambient or elevated temperature. A commercially available former (typically made of aluminum, glass, plastic, or porcelain) in the shape of the desired article is dipped into the tank and removed slowly, leaving a thin, uniform layer of the liquid elastomer solution deposited onto the former, much in the same manner that a layer of paint would be deposited upon the former if it were dipped into a container of paint. The former is dried in a stream of air to permit the solvent in the thin elastomeric layer to evaporate, at ambient temperature. The dipping procedure is repeated as necessary to build up a substrate body of the required thickness.

The substrate body is dipped into a solution of the mid block unsaturated block copolymer to deposit the block copolymer onto the surface of the substrate body, numeral 52. The preferred S-I-S mid block unsaturated block copolymer is dissolved into a solvent such as toluene in a dilute concentration, preferably about 4 percent by weight. In practice, the outside of the article is coated, and later turned inside out.

The solvent in which the S-I-S block copolymer is dissolved is removed, numeral 54, preferably by air drying.

The layer of mid block unsaturated block copolymer is chlorinated, numeral 56. Any operable chlorinating approach may be used. A number of operable techniques utilized by the inventors are described in the subsequent examples. The most preferred chlorination procedure is that discussed below in Example 8.

Optionally, the surfactant layer 32 is applied overlying the donning layer, numeral 58. When this option is used, a solution of the operable surfactant, such as 0.5 percent aqueous solution of cetyl pyridinium chloride or sodium lauryl sulfate, is prepared, and the surface of the article having the donning layer is contacted to the solution for about 15 seconds at ambient temperature.

The following examples illustrate the practice of the invention, but should not be interpreted as limiting the invention in any respect. For all of these examples, the substrate body is an S-EB-S dip-formed glove prepared according to the approach described above and in U.S. Pat. Nos. 5,112,900 and 5,407,715. These studies were performed to validate the powder-free donning approach of the invention, and there was no attempt to optimize the performance of the gloves or to meet commercial standards.

The following examples are presented to illustrate aspects of the present invention, and should not be interpreted as limiting of the invention in any respect.

EXAMPLE 1

A Glove was dip formed from S-EB-S block copolymer, as described above. While still on the former but after drying, the glove was dipped into a 4 percent by weight solution of Vector® 511 S-I-S block copolymer in toluene. The S-I-S solution on the glove was air dried to remove the solvent. The glove was dipped into a solution of 4905 grams of water, 70 grams of sodium hypochlorite (14 percent by weight in water), and sufficient hydrochloric acid to produce a solution having a pH of 2, for a period of about 15 minutes, and dried. The glove was then stripped from the former. It showed good dry donning characteristics without the use of any powder.

EXAMPLE 2

Example 1 was repeated, except that the chlorinating solution contained 4050 grams of water, 700 grams of sodium hypochlorite, and 250 grams of hydrochloric acid, and the immersion time was 1 minute. After drying and removing from the form, the glove showed good dry donning characteristics without the use of any powder.

EXAMPLE 3

Example 1 was repeated for a batch of 20 gloves, for the dip forming and S-I-S coating steps (but not for the chlorinating step, which was accomplished by a different approach as described subsequently). Before stripping the gloves from their forms, dry cornstarch powder was applied. The powdered gloves were loaded into a washing machine with 11.4 grams of Surfynol TG® mixed into 38 liters of water. The gloves were run in the washing machine for 15 minutes at low agitation and removed from the washer. The washer was then filled with a solution of 38 liters of clean water, 1994 grams of 7 percent chlorox bleach (2300 ppm chlorine), and 460 milliliters of 6N sulfuric acid, the solution having a pH of 2.2 at 18.9° C. The wet gloves were added with the S-I-S coating on the outside of the gloves and agitated for 15 minutes. The measured pH of the solution rose to 2.41 in 5 minutes, 2.64 after 10 minutes, and 2.68 after 15 minutes. After 15 minutes, the solution was neutralized with 180 milliliters of 3N potassium hydroxide to a pH of 7.02, and the gloves were further agitated for 15 minutes and removed. The gloves were rinsed with fresh cold water with 5 minutes of agitation, rinsed again with fresh cold water for 5 minutes of agitation. The gloves were removed from the washing machine, dried on low for 40 minutes, inverted, and dried on low for another 10 minutes. The powder-free gloves produced showed good dry donning characteristics with a slight yellowish color.

EXAMPLE 4

Example 3 was repeated, except that the SIS-containing Vector$^R$ 511 solution was 3 percent by weight rather than 4 percent by weight as in Example 3. The finished gloves were gamma sterilized in their packages at 2.5 Mrad dose. Control specimens with the powder coating were retained, and some of these specimens were also packaged and gamma sterilized. Samples of powder-coated and SIS-coated and chlorinated gloves were aged at 70° C. for 166 hours. Specimens for mechanical testing were retained at the various stages. Mechanical testing was performed, with the following results:

| Specimen | 500% Modulus (MPa) | Tensile Strength (MPa) | Elongation (%) |
|---|---|---|---|
| Example 4 sterilized | 3.14 | 23.36 | 942 |
| Example 4 sterilized + aged | 3.20 | 21.94 | 934 |
| Powdered and sterilized | 3.05 | 25.22 | 959 |
| Powdered and sterilized + aged | 3.6 | 28.19 | 913 |

EXAMPLE 5

A batch of 8 pairs of gloves were prepared in the manner described in Example 3, for the dip forming and S-I-S coating steps (but not for the chlorinating step, which was accomplished by a different approach as described subsequently). Before stripping the gloves from their forms, precipitate calcium carbonate powder was applied to prevent sticking. The stripped gloves were placed into a washing machine containing a pH 2.03 solution of 38 liters of water, 1994 grams of sodium hypochlorite, and 710 milliliters of 6N sulfuric acid. The gloves were agitated in the solution for 15 minutes, during which time the pH rose from 2.03 to 2.26. The solution was then neutralized with 450 milliliters of 3N potassium hydroxide to a pH of 7.05. The water solution was drained and the gloves spun in the washer for 3 minutes, rinsed twice with water for 3 minutes each, and dried in a drying on low setting for 40 minutes. The gloves were inverted and dried for an additional 15 minutes. The gloves had a light yellow color and showed good dry donning characteristics without the application of powder. The samples showed very little blocking on the S-EB-S (substrate body) side, and no blocking on the chlorinated S-I-S (donning layer) side after heat aging at 60° C. for 14 hours in the package, under a weight of 50 pairs of gloves.

EXAMPLE 6

A batch of 64 pairs of gloves were prepared in the manner described in Example 5, for the dip forming and S-I-S coating steps (but not for the chlorinating step, which was accomplished by a different approach as described subsequently). The stripped gloves were placed into a washing machine containing a pH 2.01 solution of 38 liters of water, 2294 grams of sodium hypochlorite, and 650 milliliters of 6N sulfuric acid. After the gloves were added, the pH rose to 2.31, and sufficient 6N sulfuric acid was added to bring the pH to 2.28. The gloves were agitated in the solution for 15 minutes. The solution was then neutralized with 500 milliliters of 3N potassium hydroxide to a pH of 7.55. The water solution was drained and the gloves spun in the washer for 3 minutes and rinsed twice with water for 15 minutes each.

Twenty-five pairs of the gloves were thereafter dried at 130° F. for 40 minutes, inverted, and dried for another 20 minutes. The gloves showed good dry donning characteristics and fair wet/damp donning characteristics.

Fourteen pairs of the gloves were rinsed in an aqueous solution of 0.25 weight percent cetyl pyridinium chloride and 0.05 weight percent Dow Corning silicone emulsion DC365, and dried at 130° F. for 40 minutes, inverted, and dried for another 20 minutes. The gloves had wet/damp donning characteristics superior to the samples that were untreated with the cetyl pyridinium chloride/silicone emulsion solution.

Twenty-five pairs of the gloves were rinsed in an aqueous solution of 0.5 weight percent cetyl pyridinium chloride and 0.1 weight percent Dow Corning silicone emulsion DC365, and dried at 130° F. for 40 minutes, inverted, and dried for another 20 minutes. These gloves had good dry donning characteristics, and improved wet donning characteristics compared to the gloves of the other two groups of this Example 6. However, there was a sensation of a slight soapy residue in the interior of the gloves.

All samples showed reduced blocking tendencies on the S-EB-S (substrate body) side after 60° C. aging in the package under a weight of 50 pairs of gloves, with the improvement greatest for the gloves treated with the cetyl pyridinium chloride/silicone emulsion solution.

EXAMPLE 7

A batch of 63 pairs of gloves were prepared in the manner described in Example 3, for the dip forming step (but not for the SIS-treatment or chlorinating steps, which were accomplished by a different approach as described subsequently). The S-I-S treatment was performed as in Example 3, except that the solution was 4 percent by weight of Vector® 4111 in toluene. The samples were dusted with precipitated calcium carbonate before stripping them from the formers. The gloves were chlorinated by loading them into a washing machine having a pH 2.01 solution of 38 liters of water, 2294 grams of Chlorox® bleach, and 650 milliliters of 6N sulfuric acid. After the gloves were loaded and subjected to mild agitation, the pH rose to 2.31. An additional 75 grams of sulfuric acid was added to reduce the pH to 2.28. The gloves were agitated for 15 minutes, the solution was neutralized to pH 7.15 by adding 500 milliliters of 3N potassium hydroxide, the solution was drained, and the gloves were rinsed with water twice for 15 minutes each time.

One set of 21 pairs of gloves, termed group 7-1, were dried at 130° F. for 40 minutes, inverted, and dried for another 20 minutes.

A second set of 21 pairs of gloves, termed group 7-2, were coated on their insides with a solution of 1984 grams of water, 10 grams of cetyl pyridinium chloride, and 5.7 grams of Dow Corning silicone DC 365 and dried as for the group 8-1 gloves.

A third set of 21 pairs of gloves, termed group 7-3, were rinsed with a solution of 666.7 grams of the solution prepared for the group 7-2 gloves diluted with 666.7 grams of water, and dried as for the group 7-1 gloves.

All three groups exhibited good dry donning characteristics, and the gloves of groups 7-2 and 7-3 showed good dry, wet, and damp donning characteristics.

The gloves of group 7-1, after sterilization, showed a tensile strength of 23.39 MPa and an elongation at break of 865%. The samples did not show any significant change in properties after heat aging at 70° C. for 166 hours.

The gloves of group 7-3 after aging for 20 minutes in an ozone chamber at about 250 ppm (parts per million) of ozone showed a tensile strength of 27.79 MPa and an elongation at break of 881%.

All samples showed a residue of less than 2 milligrams per glove when the residue was determined by rinsing the gloves with 150 milliliters of de-ionized water and determining the dried residue after filtration using a 3 micron nitrocellulose filter.

In a second embodiment of the invention, the substrate body 24 may be as described for the first embodiment, preferably a synthetic elastomer such as the S-EB-S block copolymer material described above, which description is incorporated here. The substrate body 24 may also be other natural and synthetic materials, for example, natural rubber latex, nitrile, isoprene rubber, S-I-S (styrene-isoprene-styrene) block copolymer, S-B-S (styrene-polybutydiene-styrene) block copolymer, S-I (styrene-isoprene) block copolymer, S-B (styrene-butadiene) block copolymer, or composition blends thereof.

Figure 5A:
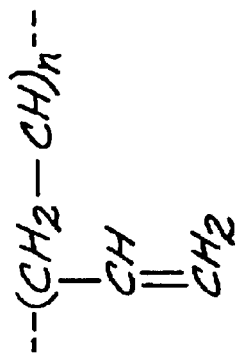
Figure 5B:
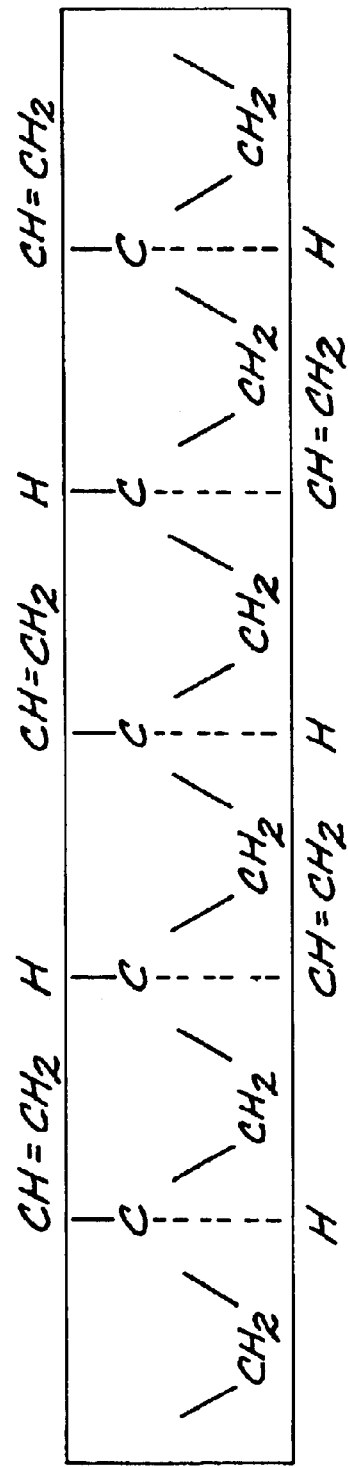

The donning layer 30 comprises 1,2 polybutadiene, whose chemical structure is depicted in FIG. 5A. Most preferably, the donning layer 30 is syndiotactic 1,2 polybutadiene, whose chemical structure is depicted in FIG. 5B. This donning layer material is chlorinated.

The surfactant layer 32, where used, is the same as described above for the first embodiment, which description is incorporated here.

The procedure used to prepare the articles is substantially as shown in FIG. 4, whose above description is incorporated here, with the following changes and details of the process. The substrate body is dip formed from an operable material such as one of the above-listed materials, numeral 50. The substrate is dipped into the donning layer solution, numeral 52. Where the substrate body is the synthetic elastomer, the substrate base is dipped into a solution of the 1,2 polybutadiene, preferably the syndiotactic 1,2 polybutadiene. The solution preferably contains from about 2 percent to about 7 percent (w/w), most preferably from about 3 percent to about 4 percent, of the 1,2 polybutadiene in an operable solvent, such as toluene. Where the substrate body is the natural rubber latex, the donning layer material is preferably prepared as an emulsion, by combining a solution of syndiotactic 1,2 polybutadiene with an ionic surfactant and water. The syndiotactic 1,2 polybutadiene is dissolved in toluene at from about 5 to about 14, preferably about 9, percent by weight. The surfactant mixture is sodium dioctyl sulfosuccinate in an amount of from about 10 to about 100, preferably 50, PHR (parts per hundred, rubber) in water. Pre-dispersion is achieved by dispersing the surfactant mixture and syndiotactic 1,2 polybutadiene solution using a high shear mixer. The pre-dispersion is then mixed for about 5 minutes in a rotor/stator (such as a Ross X Series) mixer to generate an average particle size of less than about 1 micrometer. The resulting emulsion is filtered and the solvent removed by vacuum distillation. The concentration in the final emulsion is diluted for application to the glove. The concentration of the emulsion is from about 3 to about 7 percent syndiotactic 1,2 polybutadiene in water at the time of application. After the solution or emulsion is deposited onto the substrate base, the solvent is removed, numeral 54. The donning layer is chlorinated, numeral 56, for example by the procedure discussed below in Example 8.

The surfactant layer is applied, numeral 58, by contacting a solution of the surfactant material to the exposed surface of the donning layer. The solution preferably contains from about 0.2 percent to about 1.4 percent (w/w), most preferably from about 0.7 percent to about 1 percent, of the alkyl dimethylbenzyl quaternary, alkyl trimethyl quaternary, dialkyl dimethyl quaternary, pyridinium chloride, or sodium lauryl sulfate in an operable solvent, such as water. When the polydimethyl siloxane emulsion is used in combination with the surfactant material, the concentration is from about 0.08 percent to about 0.12 percent in water.

EXAMPLE 8

Glove formers were dipped into a 1 percent solution of Presto Products "Compata Bag" dissolved in toluene. "Compata Bag" is a commercial product comprising syndiotactic 1,2 polybutadiene mixed with other ingredients including talc, erucamide, steramide. The former with the "Compata Bag" layer was air dried to remove the solvent. The substrate material of S-EB-S was then applied by overdipping the "Compata Bag" layer with sufficient dips to provide the desired thickness. While still on the former, the gloves were again dipped into a 1 percent solution of "Compata Bag" dissolved in toluene, and air dried to remove the solvent. Before stripping, calcium carbonate was applied to the outer surface. The gloves were removed from the formers and prepared for chlorination.

A washing machine was filled with 38 liters of water, 1050 milliliters of 7 percent Chlorox™ bleach (1100 parts per million chlorine) and 425 milliliters of 20 percent sulfuric acid, the solution having a pH of 2.0 at 19.5° C. With the donning surface of the outside, the powdered gloves were added to the chlorine and acid solution and agitated for 10 minutes, during which time the pH rose from 2.01 to 2.08. After 10 minutes the solution was neutralized with 60 milliliters of 50 percent potassium hydroxide to a pH of 7.76, and the agitation was continued for an additional 15 minutes.

The chlorine was neutralized from the solution and the pH buffered to maintain neutral pH by adding 325 milliliters of 6 percent hydrogen peroxide and 325 milliliters of 10 percent sodium bicarbonate solution with a resulting pH of 7.0. The gloves were rinsed with fresh water with 15 minutes of agitation, and rinsed again with fresh cold water with 15 minutes of agitation. After draining the final rinse water, the gloves were rinsed and agitated for 5 minutes in an aqueous solution of 1.0 weight percent Varisoft BTMS and 0.1 weight percent GE silicone AF60. They were then dried for 60 minutes, reaching a maximum cycle temperature of 123.3° F., then inverted and dried for an additional 40 minutes, reaching a maximum cycle temperature of 130.4° F. The resulting gloves exhibited excellent dry donning characteristics and good damp/wet donning characteristics.

EXAMPLE 9

Example 8 was repeated, but using a 2 percent solution of "Compata Bag" in toluene instead of the 1 percent solution. The powder-free gloves produced showed excellent dry and damp/wet donning characteristics.

EXAMPLE 10

Example 8 was repeated, but using a 3 percent solution of Presto "Compata Bag" in toluene instead of the 1 percent solution. The powder-free gloves produced showed excellent dry and damp/wet donning characteristics.

EXAMPLE 11

Example 10 was repeated, using a 3 percent solution of Presto "Compata Bag" in toluene. To the solution were added 10 percent calcium carbonate, 2 percent erucamide, and 2 percent steramide. The resulting powder-free gloves exhibited very good dry donning characteristics and good damp/wet donning characteristics.

EXAMPLE 12

Example 10 was repeated, using a 3 percent solution of Presto "Compata Bag" in toluene. To the solution were added 20 percent ethylmethacrylate, 2 percent erucamide, and 2 percent steramide. The resulting powder-free gloves exhibited very good dry donning characteristics and good damp/wet donning characteristics.

EXAMPLE 13

Examples 8–10 were repeated, using pure syndiotactic 1,2 polybutadiene in place of Presto Products "Compata Bag", which has additional ingredients as discussed above. The resulting gloves exhibited excellent dry and damp/wet donning characteristics. Some typical physical properties are set forth in the following table.

| Specimen | Ultimate Tensile Strength (MPa) | Tensile Modulus at 500 percent elongation (MPa) | Ultimate Elongation (percent) |
| --- | --- | --- | --- |
| Example 13, with 1 percent syndiotactic 1,2 polybutadiene, sterilized | 21.08 | 2.76 | 933 |
| Example 13, with 2 percent syndiotactic 1,2 polybutadiene, sterilized | 21.78 | 2.79 | 992 |
| Example 13, with 3 percent syndiotactic 1,2 polybutadiene, sterilized | 21.78 | 2.80 | 973 |
| Example 13, with 1 percent syndiotactic 1,2 polybutadiene, sterilized and aged | 20.50 | 2.76 | 968 |
| Example 13, with 2 percent syndiotactic 1,2 polybutadiene, sterilized and aged | 21.26 | 2.60 | 968 |
| Example 13, with 3 percent syndiotactic 1,2 polybutadiene, sterilized and aged | 19.76 | 2.72 | 979 |
| Powdered S-EB-S, sterilized | 25.2 | 3.05 | 959 |
| Powdered S-EB-S, sterilized and aged | 28.19 | 3.6 | 913 |

EXAMPLE 14

Example 8 was repeated, using a 2 percent solution of Firestone Diene 645 in toluene, instead of the Presto Products "Compata Bag". Firestone Diene 645 comprises 1,2 polybutadiene, but not in the syndiotactic form. The resulting powder-free gloves exhibited fair dry donning characteristics.

The following examples illustrate the operability of the surfactant materials.

EXAMPLE 15

Chlorinated gloves were prepared having an S-EB-S substrate and an S-I-S wash coat as the donning surface. The gloves were rinsed in an aqueous rinse solution of 0.25 percent cetylpyridinium chloride and 0.05 percent DC-365. The resulting gloves showed good damp/wet donning characteristics. Tensile strength was, however, reduced after gamma irradiation and accelerated aging.

EXAMPLE 16

Example 15 was repeated, but using an aqueous rinse solution of 0.5 percent Ammonyx 4002 from Stepan. The resulting gloves showed good damp/wet donning characteristics. The tensile strength was retained after gamma irradiation and accelerated aging.

EXAMPLE 17

Example 15 was repeated, but using an aqueous rinse solution of 0.2 percent Ammonyx 4002, 0.5 percent BTMS from Witco, and 0.1 percent silicone from DC-365. The resulting gloves showed very good damp/wet donning characteristics.

EXAMPLE 18

Example 15 was repeated, but using an aqueous rinse solution of 1.0 percent BTMS and 0.1 percent silicone from DC-365. The resulting gloves showed excellent damp/wet donning characteristics. Tensile strength was retained through all parts of the processing, including gamma irradiation sterilization and accelerated aging.

The surfactant may also be applied without using an aqueous solution. In one alternative approach, the surfactant is applied to a carrier such as a non-woven fabric by melting the surfactant and coating it onto the carrier material. The surfactant-coated material is placed in the dryer and the surfactant is liberated during the dry cycle.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A multi-layered elastomeric article, comprising:
   a hollow substrate body including a layer made of an elastomeric material, said hollow substrate body including an inside surface and an outside surface; and
   a donning layer overlying the inside surface of the hollow substrate body, the donning layer comprising 1,2 polybutadiene.

2. The elastomeric article of claim 1, wherein the elastomeric material of the substrate body comprises a mid block saturated styrene block copolymer.

3. The elastomeric article of claim 1, wherein the elastomeric material of the substrate body comprises a styrene-ethylene-butylene-styrene block copolymer.

4. The elastomeric article of claim 1, wherein the elastomeric material of the substrate body is selected from the group consisting of natural rubber latex, nitrile, isoprene rubber, styrene-isoprene-styrene block copolymer, styrene-polybutadiene-styrene block copolymer, styrene-isoprene block copolymer, styrene-butadiene block copolymer, and composition blends thereof.

5. The elastomeric article of claim 1, further including a surfactant layer overlying the donning layer.

6. The elastomeric article of claim 1, further including a surfactant layer overlying the donning layer, the surfactant layer comprising a surfactant selected from the group consisting of a cationic surfactant and a silicone, and mixtures thereof.

7. The elastomeric article of claim 1, further including a surfactant layer overlying the donning layer, the surfactant layer comprising a surfactant selected from the group consisting of an alkyl dimethylbenzyl quaternary, an alkyl trimethyl quaternary, a dialkyl dimethyl quaternary, a pyridinium chloride, sodium lauryl sulfate, and polydimethyl siloxane emulsion.

8. The elastomeric article of claim 1, wherein the donning layer comprises a syndiotactic 1,2 polybutadiene.

9. A multi-layered elastomeric article, comprising:
   a hollow substrate body including a layer made of an elastomeric material, said hollow substrate body including an inside surface and an outside surface; and
   a donning layer overlying the inside surface of the hollow substrate body, the donning layer being formed by dipping the hollow substrate body into a solution of 1,2 polybutadiene.

10. The elastomeric article of claim 9, wherein the elastomeric material of the substrate body is selected from the group consisting of natural rubber latex, styrene-ethylene-butylene-styrene block copolymer, nitrile, isoprene rubber, styrene-isoprene-styrene block copolymer, styrene-polybutadiene-styrene block copolymer, styrene-isoprene block copolymer, styrene-butadiene block copolymer, and composition blends thereof.

11. The elastomeric article of claim 9, further including a surfactant layer overlying the donning layer.

12. The elastomeric article of claim 9, further including a surfactant layer overlying the donning layer, the surfactant layer comprising a surfactant selected from the group consisting of a cationic surfactant and a silicone, and mixtures thereof.

13. The elastomeric article of claim 9, further including a surfactant overlying the donning layer, the surfactant layer comprising a surfactant selected from the group consisting of an alkyl dimethylbenzyl quaternary, an alkyl trimethyl quaternary, a dialkyl dimethyl quaternary, a pyridinium chloride, sodium lauryl sulfate, and polydimethyl siloxane emulsion.

14. The elastomeric article of claim 9, wherein the 1,2 polybutadiene comprises syndiotactic 1,2 polybutadiene.

15. A multi-layered elastomeric article, comprising:
   a hollow substrate body including a layer made of an elastomeric material, said hollow substrate body including an inside surface and an outside surface; and
   a donning layer overlying the inside surface of the hollow substrate body, the donning layer comprising 1,2 polybutadiene, said donning layer comprising a material different than said elastomeric material.

16. An elastomeric article as defined in claim 15, wherein said donning layer comprises syndiotactic 1,2 polybutadiene.

17. A multi-layered elastomeric article as defined in claim 1, wherein said donning layer is chlorinated.

18. A multi-layered elastomeric article as defined in claim 9, wherein said donning layer is chlorinated.

19. A multi-layered elastomeric article as defined in claim 15, wherein the said donning layer is chlorinated.

20. A multi-layered elastomeric article as defined in claim 1, wherein the article is a glove.

21. A multi-layered elastomeric article as defined in claim 9, wherein the article is a glove.

22. A multi-layered elastomeric article as defined in claim 15, wherein the article is a glove.

* * * * *

UNITED STATES PATENT AND TRADEMARK OFFICE
CERTIFICATE OF CORRECTION

PATENT NO. : 6,730,380 B2  
APPLICATION NO. : 09/133056  
DATED : May 4, 2004  
INVENTOR(S) : Kermit R. Littleton et al.

It is certified that error appears in the above-identified patent and that said Letters Patent is hereby corrected as shown below:

On Title Page, Item (56)  
References Cited, add --"5,492,932, Kundsin, 01/20/96"--

Signed and Sealed this

Thirtieth Day of January, 2007

JON W. DUDAS  
*Director of the United States Patent and Trademark Office*